(12) United States Patent
Haan et al.

(10) Patent No.: US 9,012,680 B2
(45) Date of Patent: Apr. 21, 2015

(54) PROCESS FOR PREPARING AN ESTER

(75) Inventors: Rene Johan Haan, Amsterdam (NL); Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 745 days.

(21) Appl. No.: 13/389,300

(22) PCT Filed: Apr. 29, 2010

(86) PCT No.: PCT/EP2010/055862
§ 371 (c)(1), (2), (4) Date: Feb. 20, 2012

(87) PCT Pub. No.: WO2011/015385
PCT Pub. Date: Feb. 10, 2011

(65) Prior Publication Data
US 2012/0190885 A1 Jul. 26, 2012

(30) Foreign Application Priority Data
Aug. 7, 2009 (EP) .................... 09167500

(51) Int. Cl.
 *C07C 67/00* (2006.01)
 *C07C 67/08* (2006.01)
(52) U.S. Cl.
 CPC ............... *C07C 67/08* (2013.01); *C07C 67/00* (2013.01)

(58) Field of Classification Search
 CPC .......... C07C 67/08; C07C 67/00; C07C 69/24
 See application file for complete search history.

(56) References Cited

U.S. PATENT DOCUMENTS

| | | | |
|---|---|---|---|
| 5,883,266 A | 3/1999 | Elliott et al. | 549/273 |
| 2010/0217038 A1* | 8/2010 | Ayoub et al. | 562/512 |

FOREIGN PATENT DOCUMENTS

| | | | |
|---|---|---|---|
| DE | 106362 | 3/1973 | .......... C07C 169/805 |
| EP | 0069409 | 1/1983 | ........... C07D 307/32 |
| WO | WO9826869 | 6/1998 | ............... B01J 23/89 |
| WO | WO02074760 | 9/2002 | ........... C07D 315/00 |
| WO | WO2006067171 | 6/2006 | ........... C07C 51/377 |
| WO | WO2008142127 | 11/2008 | .............. C07C 51/36 |

OTHER PUBLICATIONS

International Search Report (European Patent Office) for International Application PCT/EP2010/055862 dated Jun. 4, 2010; 4 pages.

\* cited by examiner

*Primary Examiner* — Joseph Kosack
*Assistant Examiner* — Matthew Coughlin

(57) ABSTRACT

A process for preparing an ester of formula (I):

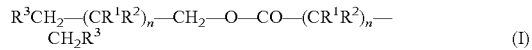

$$R^3CH_2\text{—}(CR^1R^2)_n\text{—}CH_2\text{—}O\text{—}CO\text{—}(CR^1R^2)_n\text{—}CH_2R^3 \quad (I)$$

wherein n is 1-3 and $R^1$ and $R^2$ are each, independently, a hydrogen atom or a carbon-linked organic group and $R^3$ is a carbon-linked organic group, is provided by hydrogenation of a certain lactone, carboxylic acid or its ester reactant.

14 Claims, No Drawings

PROCESS FOR PREPARING AN ESTER

PRIORITY CLAIM

The present application is a national stage entry of PCT/EP2010/055862, filed 29 Apr. 2010, which claims priority from European application 09167500.9, filed 7 Aug. 2009.

FIELD OF THE INVENTION

This invention relates to a process for preparing an ester, especially an ester that is useful as fuel component.

BACKGROUND TO THE INVENTION

Non-cyclic saturated esters are known to be useful as fuel components. Ethyl pentanoate is known as a gasoline component, for example, and pentyl pentanoate (also known as pentyl valerate) is a diesel component. Non-cyclic saturated esters of this type may be formed by hydrogenation of a reactant such as a lactone or a carboxylic acid or ester having a gamma-carbonyl group. Such reactants are available from biomass, in particular from cellulose feedstock material, rendering their use in the preparation of ester fuel components commercially attractive.

The catalytic hydrogenation of lactones, esters and carboxylic acids which have gamma-carbonyl groups using a strongly acidic heterogenous catalyst comprising a hydrogenating metal on a zeolite base is described in WO-2006/067171. This process may be used to convert gamma valerolactone (4-pentalactone or GVL) into valeric (pentanoic) acid and its esters.

Gamma valerolactone (GVL), which may itself be prepared by catalytic hydrogenation of levulinic acid or its esters, as described in WO-2006/067171, U.S. Pat. No. 5,883,266, WO-02/074760, WO-98/26869 and EP-0 069 409, is known to be a very stable compound. As described in WO-2006/067171, GVL is more easily formed under catalytic hydrogenating conditions than non-cyclic hydrogenated compounds such as pentanoic (valeric) acid or pentanoates.

Further WO-2008/142127 describes a process for converting levulinic acid into pentanoic acid comprising two hydrogenating steps. In the second hydrogenation step an effluent comprising gamma valerolactone is contacted, under hydrogenating conditions and in the presence of hydrogen, with a strongly acidic catalyst and a hydrogenation metal. In experiment 3 WO-2008/142127 describes a process wherein a feedstock of pure gamma valerolactone is reacted over a catalyst containing platinum on an acidic carrier of 25 wt % surface dealuminated ZSM-5 and 75 wt % silica binder. As illustrated in table 3, the use of a catalyst comprising Pt on an acidic carrier of surface-dealuminated ZSM-5 and silica binder results in a product composition containing mainly unconverted gamma valerolactone and pentanoic acid and only small amounts of the pentyl pentanoate ester (0.4-3.2 mol %).

There therefore remains a continuing need for an improved process to prepare esters useful as fuel components in one direct step.

SUMMARY OF THE INVENTION

The present invention provides a process for preparing an ester of formula (I):

$$R^3CH_2\text{—}(CR^1R^2)_n\text{—}CH_2\text{—}O\text{—}CO\text{—}(CR^1R^2)_n\text{—}CH_2R^2 \quad (I)$$

wherein n is 1-3 and $R^1$ and $R^2$ are each, independently, a hydrogen atom or a carbon-linked organic group and $R^3$ is a carbon-linked organic group,
by hydrogenation of a reactant selected from:
(a) a lactone of formula (II)

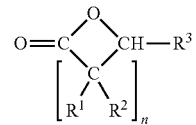

(II)

wherein n is 1-3 and $R^1$ and $R^2$ are each, independently, a hydrogen atom or a carbon-linked organic group and $R^3$ is a carbon-linked organic group;
(b) an ester of a carboxylic acid of formula (III)

$$R^4\text{—}O\text{—}CO\text{—}(CR^1R^2)_n\text{—}CO\text{—}R^3 \quad (III)$$

wherein n is 1-3 and $R^1$ and $R^2$ are each, independently, a hydrogen atom or a carbon-linked organic group and $R^3$ and $R^4$ are a carbon-linked organic group; and
c) a carboxylic acid of formula (IV)

$$H\text{—}O\text{—}CO\text{—}(CR^1R^2)_n\text{—}CO\text{—}R^3 \quad (IV)$$

wherein n is 1-3 and $R^1$ and $R^2$ are each, independently, a hydrogen atom or a carbon-linked organic group and $R^3$ is a carbon-linked organic group;
which process involves contacting the reactant with a heterogeneous catalyst comprising a hydrogenating metal in the presence of hydrogen, wherein the catalyst is a zeolite-free heterogeneous catalyst comprising a hydrogenating metal supported on a metal oxide or a mixed oxide.

DETAILED DESCRIPTION OF THE INVENTION

In the process of the invention, the reactant can for example be a lactone, a carboxylic acid having an aldehyde or ketone group in the same molecule or an ester of such a carboxylic acid.

The lactone may be of general molecular formula

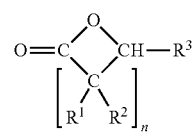

(II)

wherein n is 1-3 and $R^1$ and $R^2$ are each, independently, a hydrogen atom or a carbon-linked organic group and $R^3$ is a carbon-linked organic group. Preferably there is a proton at a carbon atom adjacent to the ring-closing carbon atom.

Preferably either $R^1$ or $R^2$ is a hydrogen atom or $R^3$ is an organic group that is connected with a proton-bearing carbon atom to the ring-closing carbon atom.

In a preferred embodiment, $R^3$ is an alkyl group. Examples of such an alkyl group include methyl, ethyl, n-propyl and isopropyl. Preferably $R^3$ is a methyl group.

Preferably n is 1 or 2, that is preferably the lactone comprises only one or two carbon atoms comprising an $R^1$ and $R^2$ Each of $R^1$ and $R^2$ at each carbon atom may differ from each other. For example the $R^1$ and the $R^2$ at a first carbon atom may be both hydrogen atoms whereas the $R^1$ and the $R^2$ at a second carbon atom may be respectively hydrogen and a carbon-linked organic group. If $R^1$ or $R^2$ is a carbon-linked organic group, $R^1$ or $R^2$ is preferably an alkyl group. Examples of such an alkyl group include methyl, ethyl, n-propyl and isopropyl.

In a preferred embodiment, $R^1$ and $R^2$ each are a hydrogen atom, more preferably $R^1$ and $R^2$ each are a hydrogen atom for all carbon atoms involved. Examples of suitable lactones are delta hexanolactone and gamma valerolactone. In one particular embodiment, the lactone is a 5-membered lactone (n is 2), especially gammavalerolactone.

A carboxylic acid having an aldehyde or ketone group in the same molecule, respectively an ester thereof, can suitably be a compound with respectively the general molecular formula IV or III.

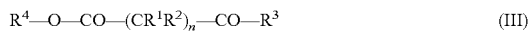
(III)

wherein n is 1-3 and $R^1$ and $R^2$ are each, independently, a hydrogen atom or a carbon-linked organic group and $R^3$ and $R^4$ are a carbon-linked organic group.

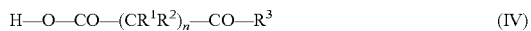
(IV)

wherein n is 1-3 and $R^1$ and $R^2$ are each, independently, a hydrogen atom or a carbon-linked organic group and $R^3$ is a carbon-linked organic group;

Preferably, $R^1$ or $R^2$ is a hydrogen atom or $R^3$ that is connected to the gamma carbon atom has a proton.

In one preferred embodiment, the reactant is a compound that is obtainable from biomass, in particular from cellulosic or lignocellulosic material. Examples of such compounds are gamma valerolactone, levulinic acid or an ester of levulinic acid (in this case $R^3$ is a methyl group, $R^1$ and $R^2$ each are a hydrogen atom and n is 2), a dimer of levulinic acid or a mono- or di-ester of such dimer. Examples of dimers of levulinic acid with a gamma carbonyl group are 4-methyl-6-oxononanedioic acid, 3-acetyl-4-methylheptanedioic acid, or their lactones, i.e. 5-(2-methyl-5-oxotetrahydrofuran-2-yl)-4-oxopentanoic acid or 3-(2-methyl-5-oxotetrahydrofuran-2-yl)-4-oxopentanoic acid.

As a product an ester of general formula (I) may be formed:

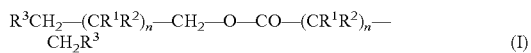
(I)

For example, where the reactant is gammavaleroactone, pentyl valerate (pentyl pentanoate) is formed.

It will be appreciated that other products such as unesterified carboxylic acids may also be formed. For example, where the reactant is gammavaleroactone, valeric acid (pentanoic acid) may be formed in addition to pentyl valerate.

Without wishing to be bound by theory, it is believed that in the process according to the invention, the reactant carboxylic acid or ester is first hydrogenated to form an acid or ester with a gamma hydroxyl group and this is then converted into a gammalactone by an internal transesterification reaction. Under the conditions of the process of the invention, the lactone thus formed (or the reactant lactone) is first converted to an unsaturated acid and then to the corresponding saturated acid (which in the case of gammavalerlactone as reactant is valeric acid). Some of this saturated acid may be further reduced to form the corresponding aldehyde or alcohol. Coupling of this aldehyde or alcohol with the saturated acid and subsequent hydrogenation leads to the formation of an ester of formula (I).

In the product the weight ratio of ester according formula (I) to unesterified carboxylic acid is preferably more than 1:5, more preferably more than 1:3, still preferably more than 1:2, and most preferably more than 2:3.

The catalyst for use in the process of the present invention is a zeolite-free heterogeneous catalyst comprising a hydrogenating metal supported on a metal oxide or a mixed oxide. The metal oxide may be a metalmonooxide or a metalpolyoxide, such as for example a metaldioxide, metal trioxide or metal pentaoxide. The mixed oxide may comprise a mixture of one or more metals and/or one or more non-metals. More preferably the catalyst is a zeolite-free heterogeneous catalyst comprising a hydrogenating metal supported on a metal dioxide.

In addition the catalyst is preferably essentially free of any other heterogeneous or homogeneous strong acidic catalyst (for example homogeneous acids having a pKa in water of less than 2), such as for example heteropolyacids or mineral acids such as sulphuric acid or phosphoric acid or any derivatives thereof. Most preferably the catalyst is a zeolite-free heterogeneous catalyst consisting essentially of a hydrogenating metal supported on a metal oxide or a mixed oxide.

In one preferred embodiment where the zeolite-free heterogeneous catalyst comprising a hydrogenating metal supported on a metal oxide (MOx), this metal oxide (MOx) has an electron-negativity EN(MOX) between 2.5 and 2.75, wherein the electron-negativity is as defined in "metal oxide chemistry and synthesis, from solution to solid state, J.-P. Jolivet, Wiley (2000)". Preferably the electron-negativety is calculated as in formula (V)

$$EN(MOx) = \Sigma(EN(i)^{(0.5)})/\Sigma(1/EN(i)^{(0.5)}) \qquad (V)$$

wherein EN(i) is the electron-negativity of the elements i (metal or oxygen) according to the Allred-Rochow scale. Without wishing to be bound by any theory, it is believed that the use of a metal oxide having such an electron-negativity results in an optimal balance between the acid and basic characteristics of the support.

In addition the energy of the metal-oxide bond in the metal oxide (MOx) is preferably more than −34 kcal per mol M-O. Preferably the energy of the metal-oxide bond in the metal oxide (MOx) is calculated as the normalized difference (D(M-O) between the heat of formation of the metal oxide (Hf(MOx)) and the heat of formation of the reduced metal oxide (Hf(MOy), that is as in formula (VI):

$$D(M-O) = [Hf(MOx) - Hf(MOy)]/2[x-y] \qquad (VI)$$

In another preferred embodiment the metal oxide or mixed oxide is chosen from the group consisting of $TiO_2$, $ZrO_2$, $Nb_2O_5$, $NbO_2$, $SnO_2$, $MoO_2$, $WO_2$, $HfO_2$, $V_2O_3$, $Cr_2O_3$, $Ga_2O_3$, $Ta_2O_5$, $CeO_2$, $MnO_2$, $ZnO_2$, $In_2O_3$, and more preferably from the group consisting of $TiO_2$, $ZrO_2$, $Nb_2O_5$, $NbO_2$, $SnO_2$, $MoO_2$, $WO_2$, $HfO_2$, $V_2O_3$, $Cr_2O_3$, $Ga_2O_3$ and $Ta_2O_5$.

It is herewith noted that $TiO_2$ (having an EN(MOx)=2.52 and a D(M-O)=−42.8); $ZrO_2$ (having an EN(MOx)=2.50 and a D(M-O)=−65.8); $NbO_2$ (having an EN(MOx)=2.60 and a D(M-O)=−47.6); and $Nb_2O_5$ (having an EN(MOx)=2.71 and a D(M-O)=−36.7) all have the preferred EN(MOx) and the preferred D(M-O), whereas $SiO_2$ (having an EN(MOx)=2.77 and a D(M-O)=−54.4); and $Al_2O_3$ having an (EN(MOx)=2.47 and a D(M-O)=−66.7) do not have the preferred EN(MOx.)

Most preferably the metal oxide or mixed oxide support is an oxide or mixed oxide of a metal selected from titanium, zirconium and niobium. In one preferred embodiment, the support is therefore a mixed oxide of titanium, zirconium or niobium, for example Nb-, Ti- and Zr-phosphates or Ti-niobate.

In a preferred embodiment, the support is a metal oxide such as $Nb_2O_5$, more preferably a metal dioxide such as $TiO_2$ or $ZrO_2$. Most preferably, the metal dioxide comprises titanium dioxide ($TiO_2$). Any titanium oxide is preferably in anatase form.

The support can be doped with a metal, preferably with a metal selected from niobium, molybdenum and tungsten.

The hydrogenating metal of the catalyst suitably comprises a metal of any one of groups 7 to 11 of the Periodic Table of Elements, such as Ni, Rh, Pd, Pt, Re, Ru, Ir or a combination of two or more thereof.

Preferably, the hydrogenating metal comprises Pt, Pd or a combination thereof, optionally additionally with one or more other metals from groups 7-11 of the Periodic Table of Elements. Most preferably, the hydrogenating metal comprises Pd.

The concentration of the hydrogenating metal based on the total weight of the catalyst will preferably be in the range of from 0.05 to 5 wt %, more preferably from 0.1 to 2 wt %.

The process of the invention is conveniently conducted at a temperature in the range of 150-450° C., suitably 200-400° C., particularly 250-350° C. It will be appreciated that the temperature may be varied depending on the metals present in the catalyst and the support used.

The process of the invention may be performed at any suitable pressure provided that it is low enough to avoid condensation of the heaviest feed component at the temperature chosen. The reactant is suitably contacted with the catalyst at a pressure of 1-150 bar (absolute). In one embodiment, the process is conducted at a pressure of 2-50 bar.

Throughout the description and claims of this specification, the words "comprise" and "contain" and variations of the words, for example "comprising" and "comprises", mean "including but not limited to", and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects. Other features of the present invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith.

Moreover unless stated otherwise, any feature disclosed herein may be replaced by an alternative feature serving the same or a similar purpose.

EXAMPLES

The invention will now be further illustrated by means of the following non-limiting examples.

Example 1

Catalyst Preparation

Various zeolite-free catalysts of the invention having a hydrogenating metal supported on a metal dioxide were prepared using an incipient wetness impregnation procedure as described below. The catalysts prepared were $0.1PdTiO_2$, $0.3PdTiO_2$, $1.0PdTiO_2$, $0.3PtTiO_2$, $1.0PtTiO_2$ (the numbers represent the metal loading in w %)

Reference catalysts, 0.7% Pt/H-ZSM-5/$SiO_2$ (H-ZSM-5 is a commercially available zeolite) and PtPd/ASA (amorphous silica alumina) were also prepared using the same procedure.

Before impregnation, the supports were pre-dried at 300° C. for 1 hour. The required amount of metal solution was calculated and prepared based on the pore volumes of the supports and the desired metal loading such that the total volume of the solution for impregnation was enough to fill 95%+/−5% of the support pores. The impregnated catalyst was subsequently calcined at 400-600° C. in air for 3 h.

The commercially available support $TiO_2$(P25, from Degussa) was used. Metal salts used were $H_2PtCl_6*6H_2O$ and $(NH_3)_4Pd(NO_3)_2$ Example 2

Gammavalerolactone (GVL) was catalytically reduced using a process according to the present invention.

The experiments were carried out using a 16-barrel microflow unit that was equipped with SS316 reactors. 0.5 g catalysts were loaded in the reactors as powder. All catalysts were reduced at 400° C. for 1 h under $H_2$ flow before the start of the un. The reactors were then cooled to 250° C. and fed with a pure GVL feed (from Innochem) and $H_2$ under the conditions specified in Tables 1 and 2 below (WHSV is weight hourly space velocity, GHSV is gas hourly space velocity, TOS is time on stream).

The % conversion of the GVL was monitored, providing an indication of the stability of catalyst activity. Also monitored was the percentage of the desired reaction product pentyl valerate (PV), valeric acid (VA) and various by-products, as an indicator of catalyst selectivity.

The data show that the desired ester product, pentyl valerate, was obtained in significant yield under a range of conditions. In general the % conversion of gamma valerolactone was higher for the Pd/TiO2 catalyst systems than for the Pt/$TiO_2$ systems, and was higher when the catalysts were calcined at 400° C. rather than 600° C.

The combined yield of pentyl valerate and valeric acid relative to other products was generally better for the Pd based catalysts rather than the Pt based catalysts, as was the yield of pentyl valerate individually. However the ratio of pentyl valerate to valeric acid was higher when the Pt-based catalysts were used.

TABLE 1

Using Pd or Pt supported on TiO2, calcined at 600° C. and reduced at 400° C.; 0.5 g catalyst; operation at 250-275-300-250° C., 10 bar H2, WHSV = 2/h; GHSV = 4500/h

| TOS [h] | T [° C.] | Conv. GVL [w %] | Selectivity [w %] PV [w %] | VA [w %] | Rest[w %] |
|---|---|---|---|---|---|
| | | 0.1PdTiO2 | | | |
| 5 | 250 | 19 | 22 | 42 | 36 |
| 10 | 275 | 36 | 24 | 34 | 42 |
| 14 | 300 | 57 | 22 | 39 | 39 |
| 24 | 250 | 19 | 16 | 49 | 35 |
| | | 0.3PdTiO2 | | | |
| 5 | 250 | 25 | 24 | 32 | 44 |
| 10 | 275 | 52 | 26 | 29 | 45 |
| 14 | 300 | 77 | 32 | 28 | 40 |
| 24 | 250 | 25 | 20 | 44 | 35 |

TABLE 1-continued

Using Pd or Pt supported on TiO2, calcined at 600°
C. and reduced at 400° C.; 0.5 g catalyst; operation
at 250-275-300-250° C., 10 bar H2, WHSV = 2/h; GHSV = 4500/h

| | | Conv. | Selectivity [w %] | | |
|---|---|---|---|---|---|
| TOS [h] | T [° C.] | GVL [w %] | PV [w %] | VA [w %] | Rest[w %] |
| 1.0PdTiO2 | | | | | |
| 5 | 250 | 17 | 19 | 31 | 51 |
| 10 | 275 | 33 | 26 | 32 | 42 |
| 14 | 300 | 57 | 32 | 29 | 39 |
| 24 | 250 | 15 | 23 | 44 | 33 |
| 0.3PtTiO2 | | | | | |
| 5 | 250 | 10 | 16 | 29 | 55 |
| 10 | 275 | 17 | 15 | 20 | 65 |
| 14 | 300 | 22 | 22 | 31 | 47 |
| 24 | 250 | 8 | 21 | 30 | 49 |
| 1.0PtTiO2 | | | | | |
| 5 | 250 | 17 | 10 | 12 | 77 |
| 10 | 275 | 31 | 13 | 10 | 78 |
| 14 | 300 | 29 | 28 | 22 | 50 |
| 24 | 250 | 16 | 15 | 15 | 69 |

TABLE 2

Using Pd or Pt supported on TiO2, calcined at 400°
C. and reduced at 400° C.; 0.5 g catalyst; operation
at 250-275-300-250° C., 10 bar H2, WHSV = 2/h; GHSV = 4500/h

| | | Conv. | Selectivity | | |
|---|---|---|---|---|---|
| TOS[h] | T[° C.] | GVL[w %] | PV{w %] | VA[w %] | Rest[w %] |
| 0.1PdTiO2 | | | | | |
| 5 | 250 | 18 | 25 | 69 | 7 |
| 10 | 275 | 46 | 25 | 47 | 28 |
| 14 | 300 | 76 | 27 | 40 | 33 |
| 24 | 250 | 21 | 22 | 67 | 11 |
| 0.3PdTiO2 | | | | | |
| 5 | 250 | 43 | 30 | 47 | 23 |
| 10 | 275 | 78 | 36 | 31 | 34 |
| 14 | 300 | 96 | 32 | 23 | 45 |
| 24 | 250 | 49 | 22 | 46 | 32 |
| 1.0PdTiO2 | | | | | |
| 5 | 250 | 77 | 26 | 31 | 43 |
| 10 | 275 | 95 | 27 | 23 | 49 |
| 14 | 300 | 100 | 9 | 10 | 82 |
| 24 | 250 | 71 | 25 | 41 | 34 |
| 0.3PtTiO2 | | | | | |
| 5 | 250 | 28 | 23 | 11 | 66 |
| 10 | 275 | 53 | 22 | 11 | 68 |
| 14 | 300 | 74 | 23 | 16 | 61 |
| 24 | 250 | 28 | 28 | 17 | 55 |
| 1.0PtTiO2 | | | | | |
| 5 | 250 | 54 | 18 | 8 | 73 |
| 10 | 275 | 78 | 18 | 9 | 74 |
| 14 | 300 | 96 | 11 | 8 | 81 |
| 24 | 250 | 54 | 23 | 12 | 65 |

Example 3

Again, GVL was hydrogenated using the process of the present invention. The catalyst chosen was 1% Pd/TiO2 calcined at 600° C. The results obtained for this catalyst and two reference catalysts (Pt/ZSM5/SiO2 and PtPd/ASA) over an extended run (334 h) are presented in Table 3 below. All three catalysts were reduced at 300° C.

TABLE 3

| | | Conv. | Selectivity | | |
|---|---|---|---|---|---|
| TOS[h] | T[° C.] | GVL[w %] | PV [w %] | VA[w %] | Rest[w %] |
| 1%Pd/TiO2 (3.15 g, 250 C., 10 bar, WHSV = 0.2/h; GHSV = 543/h) | | | | | |
| 6 | 250 | 70 | 25 | 31 | 44 |
| 22 | 250 | 63 | 22 | 33 | 45 |
| 54 | 250 | 53 | 20 | 37 | 42 |
| 106 | 250 | 50 | 17 | 35 | 48 |
| 206 | 250 | 41 | 15 | 42 | 43 |
| 334 | 250 | 40 | 12 | 39 | 49 |
| 0.7%Pt/H-ZSM-5/SiO2 (0.11 g, 250 C., 10 bar, WHSV = 6.9/h; GHSV = 15545/h) | | | | | |
| 6 | 250 | 79 | 3 | 86 | 11 |
| 22 | 250 | 45 | 4 | 90 | 6 |
| 54 | 250 | 29 | 0 | 83 | 17 |
| 106 | 250 | 21 | 0 | 78 | 22 |
| 206 | 250 | 18 | 0 | 70 | 30 |
| 334 | 250 | 12 | 0 | 76 | 24 |
| PtPd/ASA (0.6 g, 250 C., 10 bar, WHSV = 1.3/h; GHSV = 2850/h) | | | | | |
| 6 | 250 | 71 | 0 | 93 | 7 |
| 22 | 250 | 77 | 0 | 88 | 12 |
| 54 | 250 | 78 | 0 | 89 | 11 |
| 106 | 250 | 77 | 0 | 92 | 8 |
| 206 | 250 | 75 | 0 | 93 | 7 |
| 334 | 250 | 74 | 0 | 89 | 11 |

From the results presented in table 3 it can be seen that the catalyst according to the present invention shows good activity and good PV selectivity. Suitably, PV co-production can be increased further by recycling VA over the catalyst together with the fresh GVL feed.

The reference catalysts, by contrast, produce little or no PV.

Example 4

The following additional experiments were performed. From the results presented below it can be seen that a SiO2 support exhibits low activity and no PV production whereas when a ZrO2 support is used, significant PV production is obtained.

| Catalyst screening: 10 bar, WHSV = 1.92/h; GHSV = 4560 | | | | | |
|---|---|---|---|---|---|
| | | Conv. | Selectivity | | |
| TOS | T | GVL | PV | VA | rest |
| 0.3Pd/SiO2 | | | | | |
| 5 | 250 | 7 | 0 | 36 | 64 |
| 9.5 | 275 | 10 | 0 | 28 | 72 |
| 14 | 300 | 4 | 0 | 81 | 19 |
| 23.5 | 250 | −6 | 0 | −37 | 137 |
| 0.3Pd/ZrO2(RC-100) | | | | | |
| 5 | 250 | 12 | 0 | 30 | 70 |
| 9.5 | 275 | 13 | 16 | 49 | 36 |
| 14 | 300 | 20 | 18 | 47 | 35 |
| 23.5 | 250 | 9 | 0 | 30 | 70 |

Evaluation of TiO2 and ZrO2 supports doped with Nb, Mo and W show high level of activity and PV selectivity. This shows that further doping of the support can be beneficial. TiO2 supports are generally better than ZrO2.

Catalyst 10 bar, WHSV = 1.92/h;

| TOS | T | Conv. GVL | Selectivity PV | VA | rest |
|---|---|---|---|---|---|
| | | 0.3Pd/NbTiO2 | | | |
| 5 | 250 | 49 | 29 | 50 | 22 |
| 9.5 | 275 | 82 | 17 | 48 | 35 |
| 14 | 300 | 98 | 4 | 38 | 58 |
| 23.5 | 250 | 34 | 21 | 58 | 21 |
| | | 0.3Pd/MoTiO2 | | | |
| 5 | 250 | 36 | 25 | 27 | 48 |
| 9.5 | 275 | 70 | 21 | 19 | 60 |
| 14 | 300 | 95 | 12 | 13 | 75 |
| 23.5 | 250 | 32 | 32 | 35 | 33 |
| | | 0.3Pd/WTiO2 | | | |
| 5 | 250 | 43 | 30 | 50 | 20 |
| 9.5 | 275 | 74 | 29 | 47 | 24 |
| 14 | 300 | 96 | 18 | 29 | 53 |
| 23.5 | 250 | 41 | 19 | 56 | 25 |
| | | 0.3Pd/MoZrO2 | | | |
| 5 | 250 | 43 | 6 | 10 | 83 |
| 9.5 | 275 | 67 | 8 | 11 | 81 |
| 14 | 300 | 84 | 7 | 10 | 82 |
| 23.5 | 250 | 24 | 9 | 22 | 69 |
| | | 0.3Pd/NbZrO2 | | | |
| 5 | 250 | 30 | 24 | 31 | 45 |
| 9.5 | 275 | 47 | 23 | 34 | 43 |
| 14 | 300 | 72 | 14 | 29 | 58 |
| 23.5 | 250 | 19 | 21 | 43 | 36 |
| | | 0.3Pd/WZrO2 | | | |
| 5 | 250 | 77 | 16 | 59 | 24 |
| 9.5 | 275 | 97 | 2 | 28 | 70 |
| 14 | 300 | 99 | 0 | 16 | 84 |
| 23.5 | 250 | 47 | 11 | 78 | 11 |

Mixed oxides of Ti or Zr have also some activity for PV production, in particular Zr-phosphate and Ti-niobate. Nb-phosphate also shows activity for PV.

Catalyst screening: 10 bar, WHSV = 1.92/h; GHSV = 4560

| TOS | T | Conv. GVL | Selectivity PV | VA | rest |
|---|---|---|---|---|---|
| | | 1Pt/NbPO4 | | | |
| 5 | 250 | 22 | 5 | 68 | 28 |
| 9.5 | 275 | 50 | 9 | 71 | 20 |
| 14 | 300 | 84 | 6 | 53 | 42 |
| 23.5 | 250 | 16 | 6 | 58 | 35 |
| | | 1Pt/TiPO4 | | | |
| 5 | 250 | 14 | 0 | 94 | 6 |
| 9.5 | 275 | 42 | 1 | 79 | 21 |
| 14 | 300 | 77 | 4 | 85 | 11 |
| 23.5 | 250 | 26 | 0 | 65 | 35 |
| | | 1Pt/ZrPO4 | | | |
| 5 | 250 | 17 | 0 | 68 | 32 |
| 9.5 | 275 | 89 | 14 | 80 | 6 |
| 14 | 300 | 99 | 14 | 64 | 22 |
| 23.5 | 250 | 50 | 8 | 60 | 33 |
| | | 1Pt/TiNbO5 | | | |
| 5 | 250 | 18 | 5 | 64 | 31 |
| 9.5 | 275 | 37 | 11 | 83 | 5 |
| 14 | 300 | 74 | 12 | 75 | 13 |
| 23.5 | 250 | 19 | 6 | 61 | 32 |

We claim:

1. A process for preparing an ester of formula (I):

$$R^3CH_2-(CR^1R^2)_n-CH_2-O-CO-(CR^1R^2)_n-CH_2R^3 \quad (I)$$

wherein n is 1-3 and $R^1$ and $R^2$ are each, independently, a hydrogen atom or a carbon-linked organic group and $R^3$ is a carbon-linked organic group, by hydrogenation of a reactant selected from the group consisting of:

(a) a lactone of formula (II)

(II)

wherein n is 1-3 and $R^1$ and $R^2$ are each, independently, a hydrogen atom or a carbon-linked organic group and $R^3$ is a carbon-linked organic group;

(b) an ester of a carboxylic acid of formula (III)

$$R^4-O-CO-(CR^1R^2)_n-CO-R^3 \quad (III)$$

wherein n is 1-3 and $R^1$ and $R^2$ are each, independently, a hydrogen atom or a carbon-linked organic group and $R^3$ and $R^4$ are a carbon-linked organic group; and c) a carboxylic acid of formula (IV)

$$H-O-CO-(CR^1R^2)_n-CO-R^3 \quad (IV)$$

wherein n is 1-3 and $R^1$ and $R^2$ are each, independently, a hydrogen atom or a carbon-linked organic group and $R^3$ is a carbon-linked organic group;

wherein the reactant is contacted with a heterogeneous catalyst comprising a hydrogenating metal in the presence of hydrogen, said catalyst is a zeolite-free heterogeneous catalyst comprising a hydrogenating metal supported on a metal oxide or a mixed oxide, and wherein the product comprises ester according to formula (I) and unesterified carboxylic acid precursor in a weight ratio of ester according formula (I) to unesterified carboxylic acid precursor of more than 1:5.

2. The process of claim 1 wherein the reactant is a lactone of formula (II) and n is 2.

3. The process of claim 1 wherein the reactant is gamma-valerolactone and the ester product is pentyl valerate.

4. The process of claim 1 wherein the support is an oxide or mixed oxide of a metal selected from titanium, zirconium and niobium.

5. The process of claim 1 wherein the support comprises a metal dioxide selected from $TiO_2$ and $ZrO_2$.

6. The process of claim 1 wherein the support is doped with niobium, molybdenum or tungsten.

7. The process of claim 1 wherein the hydrogenating metal comprises a metal of any one of groups 7 to 11 of the Periodic Table of Elements.

8. The process of claim 7 wherein the hydrogenating metal comprises Ni, Rh, Pd, Pt, Re, Ru, Ir or a combination of two or more thereof.

9. The process of claim 1 wherein the concentration of the hydrogenating metal based on the total weight of the catalyst is in the range of from 0.05 to 5 wt %.

10. The process of claim 1 wherein the reactant is contacted with the catalyst at a temperature in the range of 150-450° C.

11. The process of claim 1 wherein the reactant is contacted with the catalyst at a pressure of 2-50 bar.

12. The process of claim 8 wherein the concentration of the hydrogenating metal based on the total weight of the catalyst is in the range of from 0.05 to 5 wt %.

13. The process of claim 12 wherein the reactant is contacted with the catalyst at a temperature in the range of 150-450° C.

14. The process of claim 13 wherein the support is an oxide or mixed oxide of a metal selected from titanium, zirconium and niobium.

* * * * *